United States Patent [19]
Griffith et al.

[11] Patent Number: 4,912,222

[45] Date of Patent: Mar. 27, 1990

[54] ANTIHISTAMINES RELATED TO CYPROHEPTADINE

[75] Inventors: Ronald C. Griffith, Pittsford; James J. Napier, Chili, both of N.Y.

[73] Assignee: Fisons Corporation, Rochester, N.Y.

[21] Appl. No.: 207,840

[22] Filed: Jun. 17, 1988

[51] Int. Cl.$^4$ ............................................. C07D 211/70
[52] U.S. Cl. .................................... 546/203; 546/196; 546/204
[58] Field of Search ......................... 546/203, 196, 204

[56] References Cited

U.S. PATENT DOCUMENTS

| | | | |
|---|---|---|---|
| 3,014,911 | 12/1961 | Engelhardt | 546/203 |
| 3,476,758 | 11/1969 | Fouché | 546/203 |
| 3,476,761 | 11/1969 | Fouché | 546/203 X |
| 3,806,526 | 4/1974 | Carr et al. | 546/190 |
| 3,862,173 | 1/1975 | Carr et al. | 546/213 |
| 3,878,217 | 4/1975 | Carr et al. | 546/191 |
| 4,282,233 | 8/1981 | Vilani | 546/93 X |
| 4,355,036 | 10/1982 | Villani | 546/80 X |

FOREIGN PATENT DOCUMENTS

| | | |
|---|---|---|
| 157399 | 10/1985 | European Pat. Off. |
| 2423721 | 12/1974 | Fed. Rep. of Germany |

OTHER PUBLICATIONS

*Drugs of the Future*, vol. 12, 1987, p. 544–549.
*Chem. Abstracts*, vol. 103, 1985, #10485r
E. Engelhardt et al., *J. Med. Chem.*, 1985, 8, 829.

*Primary Examiner*—Richard A. Schwartz
*Attorney, Agent, or Firm*—Seidel, Gonda, Lavorgna & Monaco

[57] ABSTRACT

4-Dibenzocycloheptenyl, 4-dibenzocycloheptyl, and 4-dibenzoxepinylpiperidine compounds possessing antihistaminic activity.

7 Claims, No Drawings

ANTIHISTAMINES RELATED TO CYPROHEPTADINE

BACKGROUND OF THE INVENTION

This invention relates to 4-dibenzocycloheptenyl, 4-dibenzocycloheptyl, and 4-dibenzoxepinylpiperidine compounds which possess antihistaminic activity with a low potential for sedation.

The utility of antihistamine compounds (histamine - $H_1$ antagonists) as a treatment for the alleviation of the symptoms of allergic disorders has been long recognized. However, due to their effects on the central nervous system, numerous side effects, most notably sedation, are observed with these agents (Douglas, W. W., in "The Pharmacological Basis of Therapeutics", 6th ed., Gilman, A. G. et al, Ed., MacMillian: New York, 1980. pp 622-632). An example of such a compound is cyproheptadine (4-(5H-dibenzo[a,d]cyclohepten-5-ylidene)-1-methylpiperidine).

BRIEF SUMMARY OF THE INVENTION

This invention provides compounds of the formula (1):

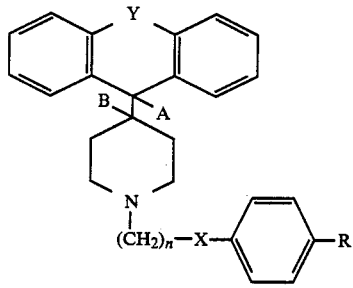

wherein n is a positive whole integer from 3 to 6; Y is —CH$_2$O—, —CH$_2$CH$_2$—, or —CH=CH—; A is hydroxy when B is hydrogen, or A and B taken together form a second bond between the carbons to which they are attached; X is —CH$_2$—, —C(=O)—, —CH(OH)—, —S—, —NH—, —O—, or —NHCH$_2$CH$_2$—; and R is hydrogen, tert—butyl, —C(CH$_3$)$_2$CH$_2$OH, —C(CH$_3$)$_2$CO$_2$H, —C(CH$_3$)$_2$COOalkyl wherein alkyl represents a chain having 1 to 4 carbon atoms, or hydrogen; with the proviso that X is —NHCH$_2$CH$_2$— when R is hydrogen.

This invention also relates to enantiomeric and diastereomeric forms and to pharmaceutically acceptable acid addition salts of the compounds of formula (1).

Preferred compounds are those in which n is 3, Y is —CH$_2$CH$_2$—, X is —CH(OH)—, and R is tert—butyl.

DETAILED DESCRIPTION OF THE INVENTION

It has now been discovered that the compounds of this invention possess antihistaminic activity with a low potential for sedation.

Some of the compounds of formula (1) above are capable of existing in enantiomeric and diastereoisomeric forms. This invention relates to all enantiomeric and diastereomeric forms of compounds of formula (1) as well as mixtures thereof.

The compounds of this invention may be prepared by several methods. Five procedures which represent the preferred methods for the preparation of the compounds of this invention are designated Methods A to E.

Method A comprises reacting an amine of formula (2):

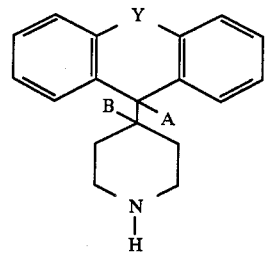

wherein Y, A and B are as described above, with an alkylation agent of formula (3):

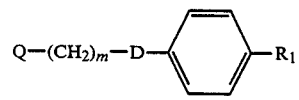

wherein Q is chlorine or bromine; m is a positive whole integer from 3 to 5; D is —CH$_2$—, —C(=O)—, —O—, —S—, or —NH—; and R$_1$ is tert—butyl or —C(CH$_3$)$_2$COOalkyl wherein alkyl represents a chain having 1 to 4 carbon atoms; said reaction being carried out in a suitable solvent, such as toluene or dimethylformamide, in the presence of a base, such as potassium bicarbonate or potassium carbonate, with or without a catalytic amount of potassium iodide, to provide the corresponding compounds of formula (1) wherein Y, A, and B are as defined above; n is a positive whole integer of 3 to 5; X is —CH$_2$—, —C(=O)—, —O—, —S—, or —NH—; and R$_1$ is tert—burtyl or —C(CH$_3$)$_2$COOalkyl wherein alkyl represents a chain having 1 to 4 carbons.

In Method B an amide bond is formed between an amine of formula (2) and a carboxylic acid of general formula (4):

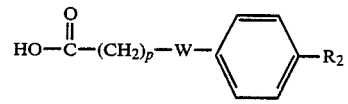

wherein p represents a positive whole integer of 2 to 4; W represents —CH$_2$—or —CONHCH$_2$CH$_2$—; and R$_2$ represents tert—butyl or hydrogen; with the proviso that W is —CONHCH$_2$CH$_2$— when R$_2$ is hydrogen, to provide an amide of general formula (5):

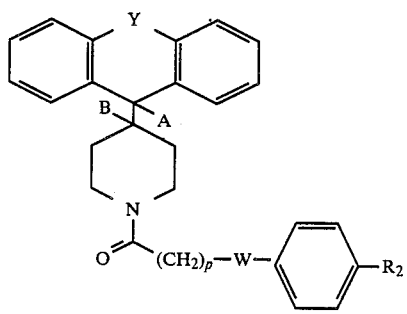

wherein Y, A, B, p, W and R$_2$ are as described above. This amide bond formation may be carried out using standard acylation methods. The preferred method is the reaction of a carboxylic acid of formula (4) with dicyclohexylcarbodiimide and 1-hydroxysuccinimide in an inert solvent, such as tetrahydrofuran, to produce the corresponding N-hydroxysuccinimide ester, which can be reacted with an amine of formula (2) in an inert solvent, such as tetrahydrofuran or dimethylformamide or mixtures thereof to produce an amide of formula (5).

Amides of formula (5) can be reacted with suitable reducing agent, such as lithium aluminum hydride, in an appropriate solvent, such as tetrahydrofuran or diethyl ether or mixtures thereof, to produce compounds of formula (1) where y, A, B and n are as defined above; X is —CH$_2$— or —NHCH$_2$CH$_2$—; and R is tert—butyl or hydrogen; with the proviso that X is —NHCH$_2$CH$_2$— when R is hydrogen.

Method C comprises reacting a compound of formula (1) where Y, A, B, and n are as defined above and R is tert—butyl or —(CH$_3$)$_2$COOalkyi, wherein alkyl represents a chain having 1 to 4 carbon atoms; and X is —C(=O)—; with a suitable reducing agent, such as sodium borohydride, in an appropriate solvent, such as a lower alkanol, for example methanol or ethanol, to provide the corresponding compounds of formula (1) wherein Y, A, B and n are as defined above and R is tert—butyl or —C(CH$_3$)$_2$COOalkyl wherein alkyl is as defined above; and X is —CH(OH)—.

Method D is useful for the preparation of compounds of formula (1) wherein Y, A, B, n and X are as defined above; and R is —C(CH$_3$)$_2$COOH. This method comprises reacting a compound of formula (1) in which R is —C(CH$_3$)$_2$COOalkyl wherein alkyl is as defined above; with an inorganic base, such as sodium hydroxide, in a lower alkanol solvent, such as ethanol or methanol, to provide the corresponding compounds of formula (1) described above.

Method E comprises reacting a compound of formula (1) where Y, A, B, n, and X are as defined above and R is —C(CH$_3$)$_2$COOalkyl wherein alkyl is as defined above; with a suitable reducing agent, such as lithium aluminum hydride, in an appropriate solvent, such as tetrahydrofuran, to provide the corresponding compound of formula (1) wherein Y, A, B, and n are as defined above; X is —CH$_2$—, —CH(OH)—, —S—, —O—, —NH—, or —NHCH$_2$CH$_2$—; and R is —C(CH$_3$)$_2$CH$_2$OH.

Compounds of the formulae (3) and (4) are known or can be made by known methods.

Many of the amines of formula (2) are known and may be prepared by suitable modification of the reported procedures. Alternatively, amines of formula (2) may be prepared by the following method: Ketones of formula (6):

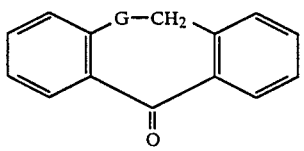

wherein G is —O— or —CH$_2$—are reacted with 4—lithiopyridine in a mixture of diethyl ether and tetramethylethylenediamine to provide the corresponding alcohols of formula (7):

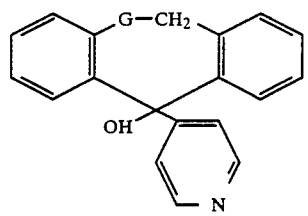

wherein G is as defined above. The compounds of formula (7) are reduced by catalytic hydrogenation in an appropriate solvent, such as acetic acid, with a suitable catalyst, such as platinum oxide, to provide the corresponding compounds of formula (2) where Y is —CH$_2$O— or —CH$_2$CH$_2$-; A is hydroxyl; and B is hydrogen.

Compounds of formula (2) where A is hydroxyl, B is hydrogen and Y is as defined above may be dehydrated to the corresponding compounds of formula (2) where A and B taken together form an additional bond between the carbons to which they are attached. This dehydration may be accomplished with a suitable acid catalyst. such as para-toluenesufonic acid, in an appropriate solvent such as chloroform.

The compounds of formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, fumaric, malic, maleic, tartaric, citric, benzoic, methanesulfonic, or carbonic acid.

The compounds of formula (1) possess antihistaminic properties and show a low potential for sedation.

Antihistaminic activity is measured by the compounds ability to inhibit the wheal response to histamine in a rat dermal vascular permeability test. Groups of 10 male rats are administered the test compound orally one hour prior to an intravenous injection of 1 mL of a 0.5% Evans Blue dye into naive animals. Ten minutes later the animals are challenged by intradermal injection of 0.1 mL of solutions of histamine at 10μg, 2μg, 1 μg or 0.5 μg per 0.1 mL into separate sites on the back. Five minutes following the histamine injections the animals are killed, the skin reflected and the mean diameter of the three wheals determined. The percent inhibition is calculated as the difference in mean diameter between the control and the drug treated group divided by the control diameter times 100. Compounds of the formula (1) were active in inhibiting the wheal response due to histamine at oral doses of 1-25 mg/kg. In particular, the compound of Example 4 caused a 50% inhibition of the wheal response to the 0.5 μg histamine challenge at a dose of about 3 mg/kg.

The sedative effects of the compounds are observed by behavioral observation of groups of mice or rats. Sedative effects were generally not observed for oral doses of the compounds of formula (1) of 200 mg/kg or less.

Some of the compounds of this invention possess a long duration of action of antihistaminic activity. For example the compound of Example 2 at an oral dose of 2 mg/kg caused a 70% inhibition of the 0.5 μg histamine wheal response after 6 hours.

The following non-limiting illustrations and examples are provided to exemplify the preparation of the compounds of formula (1).

ILLUSTRATION 1

Preparation of 10,11-Dihydro-5-(4-pyridinyl)-5H-dibenzo[a,d]-cyclohepten-5-ol To a stirred solution of 4-bromopyridine (37.9 g, 0.24 mol) in anhydrous ether (475 mL) at −75° C. under a nitrogen atmosphere was added n-butyllithium (160 mL of a 1.5 M hexane solution, 0.24 mol). Tetramethylethyenediamine (36.2 mL, 0.24 mol) was added and the solution was stirred at −75° C. for 1 hour. A solution of dibenzosuberone (50.1 g, 0.24 mol) in anhydrous ether (250 mL) was added dropwise, the reaction mixture was stirred at −75° C. for 40 minutes, warmed to ambient temperature and stirred at that temperature for 1.5 hours. Water (650 mL) was added dropwise. The solid which crystallized was isolated by filtration to give 43.54 g of 10,11-dihydro-5-(4-pyridinyl)-5H-dibenzo[a,d]cyclohepten-5-ol, mp 174–177° C. Recrystallization from ethyl acetate-hexane gave material of mp 183–185° C.

ILLUSTRATION 2

Preparation of 10,11-Dihydro-5-(4-piperidinyl)-5H-dibenzo-[a,d]cyclohepten-5-ol acetic acid (1:1) salt To a solution of 10,11-dihydro-5-(4-pyridinyl)-5H-dibenzo[a,d]cyclohepten-5-ol (44.6 g, 0.155 mol) in acetic acid (700 mL) was added platinum oxide (3.5 g) and the mixture was shaken on a Parr apparatus at 55–60° C. at 45 psi of hydrogen for 16 hours. An additional portion of platinum oxide (1.5 g) was added and the mixture was shaken at 55–60° C. at 45 psi hydrogen for an additional 20 hours. The catalyst was removed by filtration and the majority of the solvent evaporated to give an oil. The above oil was crystallized from ethyl ether (600 mL) and acetone (80 mL) to give 28.8 g of 10,11-dihydro-5-(4-piperidiny)-5H-dibenzo-[a,d]cyclohepten-5-ol acetic acid (1:1) salt, mp 89–92° C. Recrystallization of the free base from ethanol gave material of mp 217–219° C.

ILLUSTRATION 3

Preparation of 4-(10,11-Dihydro-5H-dibenzo[a,d]cyclohepten-5-ylidene)piperidine hydrochloride To a stirred solution of 10,11-dihydro-5-(4-piperidinyl)-5H-dibenzo[a,d]cyclohepten-5-ol acetic acid (1:1) salt (30.35 g, 0.086 mol) in chloroform (460 mL) was added p-toluenesulfonic acid monohydrate (30.38 g, 0.160 mol) and the mixture was heated to reflux under nitrogen for 4 hours. The reaction was cooled to ambient temperature, 5% NaOH (200 mL) added, and extracted with chloroform (3 x 100 mL). The combined chloroform extracts were washed with saturated NaCl (200 mL), dried over magnesium sulfate, and the solvent removed to give 24.6 g of a yellow solid. The above solid was dissolved in methanol (200 mL) and 2-propanol (150 mL), acidified with HCl gas, and the solid which formed was isolated by filtration to give 19.6 g of 4-(10,11-dihydro-5H-dibenzo[a,d-]cycohepten-5-yidene)-piperidine hydrochloride, mp >310° C.

ILLUSTRATION 4

Preparation of 6,11-Dihydro-1[-(4-pyridinyl)dibenz[b,e]-oxepin-11-ol

By procedures essentially the same as those described in 1illustration 1, and by substituting dibenz[b,e]oxepin-11(6H)-one for dibenzosuberone; the corresponding 6,11-dihydro-11-(4-pyridinyl)dibenz[b,e]oxepin-11-ol, mp 208–209° C. (ethanol), was prepared.

ILLUSTRATION 5

Preparation of 6,11-Dihydro-11-(4-piperidinyl)dibenz[b,e]-oxepin-11-ol acetic acid (1:1) salt By procedures essentially the same as those described in Illustration 2, and by substituting 6,11-dihydro-11-(4-pyridinyl)dibenz[b,e]oxepin-11-ol for 10,11-dihydro-5-(4-pyridinyl)-5H-dibenzo[a,d]cyclohepten-5-ol; the corresponding 6,11-dihydro-11-(4-piperidinyl)dibenz[b,e]oxepin11-ol acetic acid (1:1) salt, mp 243–245° C., was prepared.

ILLUSTRATION 6

Preparation of 4-(Dibenz[b,e]oxepin-11(6H)-ylidene)piperidine hydrochloride

By procedures essentially the same as those described in illustration 3, and by substituting 6,11-dihydro-11-(4-piperidinyl)dibenz[b,e]oxepin-11-o]acetic acid salt for 10,11-dihydro-5-(4-piperidinyl)-5H-dibenzo[a,d]cyclohepten-5-ol acetic acid salt; the corresponding 4-(dibenz[b,e]oxepin11(6H)-ylidene)piperidine hydrochloride, mp >300° C. (2-propanol), was prepared.

ILLUSTRATION 7

Preparation of 6-[(2-Phenylethyl)amino]-6-oxohexanoic acid

To a stirred solution of (2-phenylethyl)amine (6.9 g, 0.06 mol) in dichloromethane (100 mL), at ambient temperature under a nitrogen atmosphere, were added triethylamine (17.2 g, 0.17 mol) and a solution of ethyl 5-(chloroformyl)pentanoate (11.02 g, 0.057 mol) in dichloromethane (50 mL). The reaction was stirred for 18 hours at ambient temperature. The reaction was washed with 1N HCl (2 x 100 mL), 2N sodium bicarbonate (2 x 100 mL), saturated NaCl, dried over magnesium sulfate and the solvent evaporated to give 16.3 g of an oil. To a stirred solution of the above oil in methanol (200 mL) was added 10% NaOH (16 mL) and the reaction was heated to reflux for 1 hour. The reaction was poured onto 10% HCl (500 mL) and extracted with chloroform (3 x 200 mL). The combined chloroform extracts were dried over magnesium sulfate and evaporated to give 12.1 g of a solid. This solid was recrystallized from ethyl acetate and hexane to provide 10.0 g of 6-[(2-phenylethyl)amino]-6-oxohexanoic acid, mp 110–111° C.

ILLUSTRATION 8

Preparation of 3-[4-(1,1-Dimethylethyl)phenoxy]-1-chloropropane

To a stirred solution of 4-tert-butylphenol (20.0 g, 0.16 mol) in acetone (500 mL) were added potassium carbonate (100 g, 0.72 mol) and 1-bromo-3-chloropropane (50.6 g, 0.33 mol). The reaction was heated to 50° C. for 18 hours. The reaction was filtered and the solvents evaporated to provide 30.3 g of 3-[4-(1,1-dimethylethyl)phenoxy]-1-chloropropane as a colorless oil; 200 MHz NMR δ 1.47 (s,9H), 2.36 (p, J=5.5Hz, 2H), 3.88 (t, J=5.5 Hz, 2H), 4.22 (t, J=5.5Hz, 2H), 7.0, 7.47 (ABq, J=9.6Hz, 4H).

ILLUSTRATION 9

Preparation of 1-[4-(1,1-Dimethylethyl)phenyl]-4-chorobutanone

This compound was prepared by suitable modification of the procedure described by Westingh, C. van der; Hermans, B.; Raeymaekers, F.; Eycken, C. van der *Ind. Chim-Belge.*, 1960, 25, 1073 as follows. To a stirred solution of 4-chlorobutyryl chloride (72.4 mL, 0.647 mol) in dichloromethane (1 L) at 5° C. under nitrogen was added aluminum chloride (94.6 g, 0.71 mol) and the mixture was stirred for 1 hour. To this mixture was added dropwise a solution of t-butylbenzene (100 mL, 0.647 mol) in dichloromethane (100 mL). The reaction was warmed to ambient temperature and stirred at that temperature overnight. The reaction was poured onto a mixture of ice (1 L) and 0.5N HCl (1 L). The phases were separated and the aqueous phase wash extracted with dichloromethane (2 x 300 mL). The combined dichloromethane extracts were washed with 5% NaOH (2 x 300 mL), saturated NaCl (250 mL), dried over magnesium sulfate and the solvent removed to give 149.8 g of an oil. This oil was crystallized from hexanes (150 mL) to provide 118.3 g of 1-[4-(1,1-dimethylethyl)-phenyl]-4-chlorobutanone, mp 46–49° C.

ILLUSTRATION 10

Preparation of 4-[4-(1,1-Dimethylethyl)phenyl]butanoic acid

This compound was prepared by suitable modification of the procedures described by Martin, E. L., *J. Am. Chem. Soc.*, 1936, 58, 1841 as follows. To a stirred suspension of aluminum chloride (266 g, 2.0 mol) in dichloromethane (1 L) cooled in an ice water bath under a nitrogen atmosphere was added succinic anhydride (100 g, 1.0 mol). The mixture was warmed to ambient temperature and a solution of t-butylbenzene (122.4 g, 0.897 mol) in dichloromethane was added dropwise. The reaction was stirred at ambient temperature for 16 hours. The reaction was poured onto 2N HCl and extracted with chloroform (2 x 800 mL). The combined organic extracts were washed with saturated NaCl, dried over magnesium sulfate and the solvent evaporated to give 156.6 g of a tan solid. Recrystallization from toluene (700 mL) and hexanes (200 mL gave 94.5 g of 4-[4-(1,1dimethylethyl)-phenyl]-4-oxobutanoic acid, mp 112–114° C.

To a stirred suspension of zinc amalgam (180 g) in water (150 mL) were carefully added conc. HCl (325 mL), toluene (150 mL), acetic acid (40 mL), and 4-[4-(1,1-dimethylethyl)phenyl]-4-oxobutanoic acid (45 g, 0.19 mol). The reaction was heated to reflux for 24 hours. The reaction was cooled to ambient temperature, the solution decanted and extracted with ether (3 x 300 mL). The combined ether extracts were washed with saturated sodium chloride (300 mL), dried over magnesium sulfate, and concentrated to give 42.2 g of an off-white solid. Recrystallization from hexanes gave 25.0 g of 4-[4-(1,1-dimethylethyl)phenyl]butanoic acid, mp 55–57° C.

ILLUSTRATION 11

Preparation of 4-[4-(1,1-Dimethylethyl)phenyl]-1-bromobutane

To a stirred suspension of lithium aluminum hydride (4.0 g, 0.105 mol) in THF (100 mL) at 0° C. under a nitrogen atmosphere was added a solution of 4-[4-(1,1-dimethylethyl)-phenyl]butanoic acid (10.31 g, 0.0455 mol) in THF (80 mL). The reaction was heated to reflux for 6 hours. The reaction was cooled to 0° C. and water (4 mL), 15% NaOH (4 mL) and water (12 mL) were carefully added. Ethyl ether (150 mL) was added, the mixture warmed to ambient temperature, and the precipitated salts were removed by filtration. Removal of solvent gave 9.15 g of 4-[4-(1,1-dimethylethyl)phenyl]-butanol as a colorless oil.

To a stirred solution of phosphorous tribromide (1.75 mL, 0.185 mol) in benzene (100 mL) at 8° C. was added a solution of 4-[4-(1,1-dimethylethyl)phenyl]butanol (9.15 g, 0.0444 mol) in benzene (50 mL). The solution was stirred at 10° C. for 2 hours, water (200 mL) was added, and the mixture was extracted with ethyl ether (2 x 150 mL). The combined ether extracts were washed with water (2 x 150 mL), saturated NaCl (150 mL) and dried over magnesium sulfate. Removal of solvent gave 11.6 g of an oil. This oil was purified by silica gel chromatography, eluting with 5% ethyl acetate-hexane, to give 3.16 g of 4-[4-(1,1-dimethylethyl)-phenyl]-1-bromobutane as a colorless oil, NMR δ 1.37 (s, 9H), 1.8 (m, 2H), 2.45 (t, J=7Hz, 2H), 3.38 (t, J=7Hz, 2H), 7.1, 7.3 (ABq, J=9.5Hz, 4H).

EXAMPLE 1

Preparation of 4-[4-(10,11-Dihydro-5H-dibenzo[a,d]cyclohepten-5-ylidene)-1-piperidinyl]-1-[4-(1,1-dimethylethyl)phenyl]-1-butanone maleate

Method A

To a stirred solution of 4-(10,11-dihydro-5H-dibenzo[a,d]cyclohepten-5-ylidene)piperidine (71.3 g, 0.249 mol) in toluene (1 L) were added 4'-tert-butyl-4-chlorobutyrophenone (91.5 g, 0.38 mol), potassium bicarbonate (53 g, 0.5 mol) and potassium iodide (2.5 g, 0.015 mol). The mixture was heated to reflux under a nitrogen atmosphere for 48 hours. The mixture was cooled to ambient temperature, poured into water (2 L), the phases separated, and the aqueous phase was extracted with chloroform (2 x 500 mL). The combined organic extracts were dried over magnesium sulfate and the solvent removed to give 172 g of an oil. The oil was dissolved in hot ethyl acetate (500 mL) and treated with maleic acid (74 g, 0.63 mol) in hot ethyl acetate (300 mL); upon cooling, a white solid crystallized and was collected by filtration to give 165.3 g. This solid was recrystallized from ethanol (800 mL) to give 110.6 g of 4-[4-(10,11-dihydro-5H-dibenzo[a,d]cyclohepten-5-ylidene)-1-piperidinyl]-1-[4-(1,1-dimethylethyl)phenyl]-1-butanone maleate, mp 178–180° C.

EXAMPLE 2

Preparation of
4-(10,11-Dihydro-5H-dibenzo[a,d]cyclohepten-5-ylidene)-1-[4-[4-(1,1-dimethylethyl)phenyl]-4-hydroxybutyl]-piperidine Method C To a stirred solution of 4-[4-4-(0,1-dihydro-5H-dibenzo-[a,d]cycohepten-5-ylidene)-1-piperidinyl]-1-[4-(1,1-dimethylethyl)phenyl]-1-butanone maleate (110.6 g, 0.22 mol) in chloroform (750 mL) and water (1 L) was added enough 15% NaOH to give a solution of pH 11. The phases were separated and the aqueous phase extracted with CHCl3 (3 x 500 mL). The combined choroform extracts were dried over MgSO4 and the solvent removed to give 96.1 g of an oil. To a stirred solution of the above oil in methanol (2 L) at 0° C. under nitrogen was added sodium borohydride (29.7 g, 0.79 mol). The reaction was allowed to warm to ambient temperature and stirred at that temperature overnight. Acetone (200 mL) was added to the reaction dropwise, and the solvents were removed. The solid residue was dissolved in water (2 L) and extracted with chloroform (3 x 750 mL). The combined chloroform extracts were dried over magnesium sulfate and the solvent removed to provide 128 g of a white so id. This solid was recrystalized from 2-propanol (750 mL) and then from 2-propanol (500 mL) and methanol (200 mL), and vacuum dried at 85° C. for 5 days to provide 64.5 g of 4-(10,11-dihydro-5H-dibenzo[a,d]cyclohepten-5-yidene)-1-[4-[4-(1,1-dimethylethyl)phenyl]-4-hydroxybutyl]piperidine, mp 157–158° C.

EXAMPLE 3

Preparation of
4-(10,11-Dihydro-5H-dibenzo[a,d]cyclohepten-5-ylidene)-1-[4-[4-(1,1-dimethylethyl)phenyl]butylpiperidine hydrochloride Method B To a stirred solution of 4-[4-(1,1-dimethylethyl)-phenyl]-butanoic acid (7.26 g, 0.033 mol) in tetrahydrofuran (145 mL) were added N-hydroxysuccinimide (3.80 g, 0.033 mo[) and dicyclohexylcarbodiimide (6.81 g, 0.033 mol). The reaction was stirred at ambient temperature under nitrogen for 21 hours. The precipitated solid was removed by filtration. To a stirred solution of the filtrate, at ambient temperature under nitrogen was added a solution of 4-(10,11-dihydro-5H-dibenzo[a,d-]cyclohepten-5-ylidene)-piperidine (9.16 g, 0.032 mol) in tetrahydrofuran (130 mL) and dimethylformamide (150 mL), and the reaction was stirred at ambient temperature for 24 hours. The solvents were removed and the residue was dissolved in chloroform (250 mL). The chloroform solution was washed with 5% NaOH (2 x 150 mL), saturated NaCl (200 mL), dried over MgSO4, and the solvent removed to provide 19.4 g of an oil. This oil was purified by silica gel chromatography on a Waters Prep 500 HPLC, eluting with ammoniated 0.5% methanol-chloroform to provide 9.80 g of 4-(10,11-dihydro-5H-dibenzo[a,d]cyclohepten-5-ylidene)-1-[4-[4-(1,1-dimethylethyl)phenyl]-1-oxobutyl]-piperidine as an oil.

To a stirred solution of the above oil in anhydrous ether (500 mL) at 0° C. under nitrogen was added lithium aluminum hydride (4.18 g, 0.11 mol). The reaction was warmed to ambient temperature and stirred at that temperature for 20 hours. The reaction was cooled to 0° C. and water (4 mL), 15% NaOH (4 mL) and water (12 mL) were carefully added. The insoluble salts were removed by filtration through celite, and the filtrate was concentrated to an oil. The above oil was dissolved in chloroform (250 mL), washed with water (250 mL), saturated NaCl (150 mL), dried over MgSO4, and the solvent removed to give 9.95 g of an oil. The above oil was dissolved in ethyl acetate (30 mL) and acidified with HCl gas, and ether (75 mL) was added. The solid was collected by filtration, recrystallized from ethyl acetate (75 mL), cyclohexane (50 mL) and methanol (5 mL), and vacuum dried at 80° C. for 9 days to provide 4.98 g of 4-(10,11-dihydro-5H-dibenzo-[a,d]cyclohepten-5-ylidene)-1-[4-[4-(1,1-dimethylethyl)-phenyl]butyl]-piperidine hydrochloride, mp 177–179° C.

EXAMPLE 4

Preparation of
4-Dibenz[b,e]oxepin-11(6H)-ylidene-1-[4-[4-(1,1-dimethylethyl)phenyl]butyl]piperidine hydrochloride To a stirred solution of 4-dibenz[b,e]oxepin-11(6H)-ylidenepiperidine (7.1 g, 0.026 mol) in dimethyformamide (70 mL) were added potassium bicarbonate (5.12 g, 0.051 mol) and a solution of 4-[4-(1,1-dimethylethyl)-phenyl]-1-bromobutane (7.6 g, 0.028 mol) in dimethylformamide (30 mL). The reaction was heated to 70° C. for 36 hours under a nitrogen atmosphere. The reaction mixture was cooled to ambient temperature, poured into water (300 mL) and extracted with ethyl acetate (2 x 200 mL). The combined ethyl acetate extracts were washed with water (3 x 150 mL), saturated NaCl, and dried over MgSO4. Removal of solvent gave 12 67 g of an oil. This oil was dissolved in ether (300 mL) and ethanol (50 mL) and acidified with HCl. The solid which formed was isolated by filtration, and vacuum dried at 80° C. for 72 hours to provide 7.61 g of 4-dibenz[b,e ]oxepin-11(6H)-ylidene-1-[4-[4-(1,1-dimethylethyl)phenyl]butyl]piperidine hydrochloride, mp 218–219° C.

EXAMPLE 5

Preparation of
4-[4-(10,11-Dihydro-5-hydroxy-5H-dibenzo[a,d]-cyclohepten-5-yl)-1-piperidinyl]-1-[4-(1,1-dimethylethyl)-phenyl]-1-butanone By procedures essentially the same as those described in Example 1, and by substituting 10,11-dihydro-5-(4-piperidinyl)-5H-dibenzo[a,d]cyclohepten-5-ol for 4-(10,11-dihydro-5H-dibenzo[a,d]cyclohepten-5-ylidene)-piperidine; the corresponding 4-[4-(10,11-dihydro-5-hydroxy-5H-dibenzo[a,d]cyclohepten-5-yl)-1-piperidinyl]-1-[4-(1,1-dimethylethyl)phenyl]-1-butanone, mp 132–134° C. (ethanol), was prepared.

EXAMPLE 6

Preparation of
4-(4-Dibenz[b,e]oxepin-11(6H)-ylidene-1-piperidinyl)-1-[4-(1,1-dimethylethyl)phenyl]-1-butanone hydrochloride By procedures essentially the same as those described in Example 1, and by substituting 4-dibenz[b,e]oxepin-11(6H)-ylidenepiperidine for 4-(10,11-dihydro-5H-dibenzo-[a,d]cyclohepten-5-ylidene)piperidine; the corresponding 4-(4-dibenz[b,e]oxepin-11(6H)-ylidene-1-piperidinyl)-1-[4-(1,1-dimethylethyl)phenyl]-1-buta-

EXAMPLE 7

Preparation of
4-Dibenz[b,e]oxepin-11(6H)-ylidene-1-[4-[4-(1,1-dimethylethyl)phenyl]-4-hydroxybutyl]piperidine By procedures essentially the same as those described in Example 2, and by substituting 4-[4-(dibenz[b,e]oxepin-11(6H)-ylidene)-1-piperidinyl]-1-[4-(1,1-dimethylethyl)-phenyl]-1-butanone hydrochloride for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 4-dibenz[b,e]oxepin-11(6H)-ylidene-1-[4-[4-(1,1-dimethyethyl)phenyl]-4-hydroxybutyl]piperidine, mp 159.5–161° C. (2-propanol), was prepared.

EXAMPLE 8

Preparation of
4,4-[(6,1.Dihydro-11-hydroxydibenz[b,e]-oxepin-11-yl)-1-piperidiny -1-[4-(1,1-dimethylethyl)-phenyl]butanone By procedures essentially the same as those described in Example 1, and by substituting 6,11-dihydro-11-(4-piperidinyl)dibenz[b,e oxepin-11-ol for 4-(10,11-dihydro-5H-dibenz[a,d]cyclohepten-5-ylidene)piperidine; the corresponding 4-[4-(6,11-dihydro-11-hydroxydibenz[b,e]-oxepin-11-yl)-1-piperidinyl]-1-[4-(1,1-dimethylethyl)phenyl]-butanone, mp 143°–145° C. (2-propanol), was prepared.

EXAMPLE 9

Preparation of
11-[1-[4-[4-(1,1-Dimethylethyl)phenyl]-4-hydroxybutyl]-4-piperidinyl]-6,11-dihydrodibenz[b,e]oxepin-11-ol By procedures essentially the same as those described in Example 2, and by substituting 4-[4-(6,1]-dihydro-11-hydroxydibenz[b,e]oxepin-11-yl)-1-piperidinyl]-1-[4-(1,1-dimethylethyl)phenyl]butanone for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 11-[1-[4-[4-(1,1-dimethylethyl)phenyl]-4-hydroxybutyl]]-4-piperidinyl]-6,11-dihydrodibenz[b,e]oxepin-11-ol, mp 135°–137° C. and 162–165° C. (ether), was prepared.

EXAMPLE 10

Preparation of
11-1-4-4-(1,1-Dimethylethyl)phenyl]butyl]-4-piperidinyl]-6,11-dihydrodibenz[b,e]oxepin-11-o By procedures essentially the same as those described in Example 4, and by substituting 6,11-dihydro-11-(4-piperidinyl)dibenz[b,e]oxepin-11-ol for 4-dibenz[b,e]oxepin-11(6H)-ylidenepiperidine; the corresponding 11-[1-[4-[4(1,1-dimethylethyl)phenyl]butyl]-4-piperidinyl]-6,11-dihydrodibenz[b,e]oxepin-11-ol, mp 140°–141° C. (2-propanol), was prepared.

EXAMPLE 11

Preparation of
10,11-Dihydro-5-[1-[4-[4-(1,1-dimethylethyl)-phenyl]-4-hydroxybutyl]-4-piperidinyl]-5H-dibenzo[a,d]-cyclohepten-5-ol By procedures essentially the same as those described in Example 2, and by substituting 4-[4-(10,11-dihydro-5-hydroxy-5H-dibenzo[a,d]cyclohepten-5-yl)-1-piperidinyl]-1-[4-(1,1-dimethylethyl)phenyl]-1-butanone for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 10,11-dihydro-5-[1-[4-[4-(1,1-dimethylethyl)phenyl]-4-hydroxybutyl]-4-piperidinyl]-5H-dibenzo[a,d]cyclohepten-5-ol, mp 142°–144° C. (ethanol-water), was prepared.

EXAMPLE 12

Preparation of
10,11-Dihydro-5-[1-[4-[4-(1,1-dimethylethyl)-phenyl]-butyl]-4-piperidinyl]-5H-dibenzo[a,d]cyclohepten-5-ol By procedures essentially the same as described in Example 4, and by substituting 10,11-dihydro-5-(4-piperidinyl)-5H-dibenzo[a,d]cyclohepten-5-ol for 4-dibenz-[b,e]oxepin-11(6H)-ylidenepiperidine; the corresponding 10,11-dihydro 5-[1-[4-[4-(1,1-dimethylethyl)-phenyl]butyl]-4-piperidinyl]-5H-dibenzo[a,d]cyclohepten-5-ol, mp 99°–101° C. (2-propanol), was prepared.

EXAMPLE 13

Preparation of
4-[4-(5H-Dibenz[a,d]cyclohepten-5-ylidene)-1piperidinyl]-1-[4-(1,1-dimethylethyl)phenyl]-1-butanone maleate By procedures essentially the same as described in Example 1, and by substituting 4-(5H-dibenzo[a,d]cyclohepten-5-ylidene)piperidine for 4-(10,11-dihydro-5H-dibenzo-[a,d]cyclohepten-5-ylidene)piperidine; the corresponding 4-[4-(5H-dibenz[a,d]cyclohepten-5-ylidene)-1-piperidinyl]-1-[4-(1,1-dimethylethyl)phenyl]-1-butanone maleate, mp 161°–162° C. (2-propanol), was prepared.

EXAMPLE 14

Preparation of
4-(5H-Dibenzo[a,d]cyclohepten-5-ylidene)-1-[4-[4-(1,1-dimethylethyl)phenyl]-4-hydroxybutyl]piperidine By procedures essentially the same as those described in Example 2, and by substituting 4-(5H-dibenzo[a,d]cyclohepten-5-ylidene)-1-piperidinyl]-1-[4-(1,1-dimethylethyl)-phenyl]-1-butanone maleate for 4-(10,11-dihydro-5H-dibenzo-[a,d]cyclohepten-5-ylidene)-1-piperidinyl]-1-[4-(1,1-dimethylethyl)phenyl]-1-butanone maleate; the corresponding 4-(5H-dibenzo[a,d]cyclohepten-5-ylidene)-1-[4-[4-(1,1-dimethylethyl)phenyl]-4-hydroxybutyl]piperidine, mp 141°–142° C. (2-propanol), was prepared.

EXAMPLE 15

Preparation of
5-[4-(10,11-Dihydro-5H-dibenzo[a,d]cyclohepten-5-ylidene)-1-piperidinyl]-1-[4-(1,1-dimethylethyl)phenyl]-1-pentanone maleate By procedures essentially the same as those described in Example 1, and by substituting 4'-tert-butyl-5-chlorovalerophenone for 4'-tert-butyl-4-chlorobutyrophenone, the corresponding 5-[4-(10,11-dihydro-5H-dibenzo[a,d]cyclo-1 hepten-5-ylidene)-1-piperidinyl]-1-[4-(1,1-dimethylethyl)-phenyl]-1-pentanone maleate, mp 140°–141° C. (2-propanol, ether), was prepared.

EXAMPLE 16

Preparation of
6-[4-(10,11-Dihydro-5H-dibenzo[a,d]cyclohepten-5-ylidene)-1-piperidinyl]-1-[4-(1,1-dimethylethyl)phenyl]-1-hexanone fumarate By procedures essentially the same as those described in Example 1, and by substituting 4'-tert-butyl-6-bromohexanophenone for 4'-tert-butyl-4-chlorobutyrophenone; the corresponding 6-[4-(10,11-dihydro-5H-dibenzo[a,d]cyclohepten-5-ylidene)-1-piperidinyl]-1-[4-(1,1-dimethylethyl)-phenyl]-1-hexanone fumarate, mp 185°–187° C. (ethyl acetate ether), was prepared.

EXAMPLE 17

Preparation of
4-(10,11-Dihydro-5H-dibenzo[a,d]cyclohepten-5-ylidene)-1-[5-[4-(1,1-dimethylethyl)phenyl]-5-hydroxypentyl]-piperidine By procedures essentially the same as described in Example 2, and by substituting 5-[4-(10,11-dihydro-5H-dibenzo[a,d]cyclohepten-5-ylidene)-1-piperidinyl]-1-[4-(1,1-dimethylethyl)phenyl]-1-pentanone maleate for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 4-(10,11-dihydro-5H-dibenzo[a,d]cyclohepten-5-ylidene)-1-[5-[4-(1,1-dimethylethyl)phenyl]-5-hydroxypentyl]-piperidine, mp 157°–158° C. (2-propanol), was prepared.

EXAMPLE 18

Preparation of
4-(10,11-Dihydro-5H-dibenzo[a,d]cyclohepten-5-ylidene)-1-[6-[4-(1,1-dimethylethyl)phenyl]-6-hydroxyhexyl]-piperidine fumarate By procedures essentially the same as described in Example 2, and by substituting 64-[4-(10,11-dihydro-5H-dibenzo[a,d]cyclohepten-5-ylidene)-1-piperidinyl]-1-[4-(1,1-dimethylethyl)phenyl]-1-hexanone fumarate for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 4-(10,11-dihydro-5H-dibenzo[a,d]cyclohepten-5-ylidene)-1-[6-[4-(1,1-dimethylethyl)phenyl]-6-hydroxyhexyl]-piperidine fumarate, mp 120°–121° C. (2-propanol, ethyl acetate), was prepared.

EXAMPLE 19

Preparation of
4-(10,11-Dihydro-5H-dibenzo[a,d]cyclohepten-5-ylidene)-1-[5-[4-(1,1-dimethylethyl)phenyl]pentyl]-piperidine fumarate By procedures essentially the same as described in Example 4, and by substituting 4-(10,11-dihydro-5H-dibenzo[a,d]-cyclohepten-5-ylidene)piperidine for 4-dibenz[b,e]oxepin-11(6H)-ylidenepiperidine and 5-[4-(1,1-dimethylethyl)phenyl]-1-bromopentane for 4-[4-(1,1-dimethylethyl)phenyl]-1-bromobutane; the corresponding 4-(10,11-dihydro-5H-dibenzo-[a,d]cyclohepten-5-ylidene)-1-[5-[4-(1,1-dimethylethyl)-phenyl]pentyl]piperidine fumarate, mp 157°–158° C., was prepared.

EXAMPLE 20

Preparation of
4-(10,11-Dihydro-5H-dibenzo[a,d]cyclohepten-5-ylidene)-1-[6-[4-(1,1-dimethylethyl)phenyl]hexyl]-piperidine maleate By procedures essentially the same as described in Example 3, and by substituting 6-[4-(1,1-dimethylethyl)-phenyl]-hexanoic acid for 4-[4-(1,1-dimethylethyl)-phenyl]butanoic acid; the corresponding 4-(10,11-dihydro-5H-dibenzo[a,d]cyclohepten-5-ylidene)-1-[6-[4-(1,1-dimethylethyl)phenyl]hexyl]piperidine maleate, mp 166°–167° C. (ethyl acetate), was prepared.

EXAMPLE 21

Preparation of
4-(10,11-Dihydro-5H-dibenzo[a,d]cyclohepten-5-ylidene)-1-[3-[4-(1,1-dimethylethyl)phenoxy]propyl 1]piperidine hydrochloride To a stirred solution of 4-(10,11-dihydro-5H-dibenzo-[a,d]cyclohepten-5-ylidene)piperidine (8.0 g, 0.029 mol) in dimethylformamide (200 mL) were added potassium carbonate (100 g, 0.72 mol) and 3-[4-(1,1-dimethylethyl)phenoxy]-1-chloropropane (9.0 g, 0.043 mol). The reaction mixture was heated to 60°–65° C. for 18 hours. The reaction was poured into water (1 L) and extracted with ethyl acetate (3 x 300 mL). The combined ethyl acetate extracts were washed with water (3 x 200 mL), saturated with NaCl (200 mL), dried over magnesium sulfate, and the solvent removed to give 16.1 g of an oil. This oil was purified by silica gel chromatography on a Waters PREP 500 HPLC, eluting with ammoniated 25% ethyl acetate-hexane, to give 5.0 g of an oil. This oil was dissolved in ethyl acetate (75 mL) and 2-propanol (5 mL) and acidified with Hi gas. The solid which formed was collected by filtration, and vacuum dried at 90° C. for 5 days to provide 3.1 g of 4-(10,11-dihydro-5H-dibenzo[a,d]cyclohepten-5-ylidene)-1-[3-[4-(1,1-dimethylethyl)phenoxy]propyl]-piperidine hydrochloride, mp 209°–210° C.

EXAMPLE 22

Preparation of
4-(10,11-Dihydro-5H-dibenzo[a,d]cyclohepten-5-ylidene)-1-[3-[[4-(1,1-dimethylethyl)phenyl thio]propyl]-piperidine fumarate By procedures essentially the same as those described in Example 21, and by substituting 3-[[4-(1,1-dimethylethyl)-phenyl]thio]-1-chloropropane for 3-[4-(1,1-dimethylethyl)-phenoxy]-1-chloropropane; the corresponding 4-(10,11-dihydro-5H-dibenzo[a,d]cyclohepten-5-ylidene)-1-[3-[[4-(1,1-dimethylethyl)phenyl]thio]-propyl]piperidine fumarate, mp 189°–190° C. (ethyl acetate, 2-propanol), was prepared.

EXAMPLE 23

Preparation of
3-[4-(10,11-Dihydro-H-dibenzo[a,d]cyclohepten-5-ylidene)-1-piperidine
-N-[4-(1,1-dimethylethyl)phenyl]-propanamine dihydrochloride By procedures essentially the same as those described in Example 4, and by substituting 4-(10,11-dihydro-5H-dibenzo[a,d]cyclohepten-5-ylidene)piperidine for 4-dibenz-[b,e]oxepin-11(6H)-ylidenepiperidine and N-(3-chloropropyl 4-(, dimethyethyl)benzeneamine for 4-[4-

(1,1-dimethylethyl)phenyl-1-bromobutane; the corresponding 3-[4-(10,11-dihydro-5H-dibenzo[a,d]cyclohepten-5-ylidene)-1-piperidinyl]-N-[4-(1,1-dimethylethyl)phenyl]propanamine dihydrochloride, mp 217°220° C. (ethyl acetate, methanol), was prepared.

EXAMPLE 24

Preparation of 4-[4-[4-(10,11-Dihydro-5H-dibenzo[a,d]cyclohepten-5-ylidene)-1-piperidinyl]-1-oxobutyl]-α,α-dimethylbenzeneacetic acid ethyl ester hydrobromide By procedures essentially the same as those described in Example 1, and by substituting 4-(4-chloro-1-oxobutyl)-α, α-dimethylbenzeneacetic acid ethyl ester for 4'-tert-butyl-4-chlorobutyrophenone; the corresponding 4-[4-[4-(10,11-dihydro-5H-dibenzo[a,d]cyclohepten-5-ylidene)-1-piperidinyl]-1-oxobutyl]-α, α-dimethylbenzeneacetic acid ethyl ester hydrobromide, mp 187°-189° C. (methanol), was prepared.

EXAMPLE 25

Preparation of 4-[4-[4-(10,11-Dihydro-5H-dibenzo[a,d]cyclohepten-5-ylidene)-1-piperidinyl]-1-hydroxybutyl]-α, α-dimethylbenzeneacetic acid ethyl ester By procedures essentially the same as those described in Example 2, and by substituting 4-[4-[4-(10,11-dihydro-5H-dibenzo[a,d]cyclohepten-5-ylidene)-1-piperidinyl]-1-oxobutyl]-α,α-dimethylbenzeneacetic acid ethyl ester hydrobromide for 4-[4-(10,11-dihydro-5H-dibenzo[a,d]cyclohepten-5-ylidene)-1-piperidinyl]-1-[4-(1,1-dimethylethyl)phenyl]-1-butanone maleate; the corresponding 4-[4-[4-(10,11-dihydro-5H-dibenzo[a,d]cyclohepten-5-ylidene)-1-piperidinyl]-1-hydroxybutyl]-α, α-dimethylbenzeneacetic acid ethyl ester, mp 142°-144° C. (ethanol-water), was prepared.

EXAMPLE 26

Preparation of 4-[4-[4-(10,11-Dihydro-5H-dibenzo[a,d]cyclohepten-5-ylidene)-1-piperidinyl]-1-hydroxybutyl]-α, α-dimethylbenzeneacetic acid Method D To a stirred suspension of 4-[4-[4-(10,11-dihydro-5H-dibenzo[a,d]cyclohepten-5-ylidene)-1-piperidinyl]-1-hydroxybutyl]-α, α-dimethylbenzeneacetic acid ethyl ester (5.62 g, 0.010 mol) in ethanol (150 mL) was added 15% NaOH (15 mL) and the mixture was heated to reflux, under nitrogen, for 2 hours. The reaction was cooled to ambient temperature, concentrated to approximately ½ its original volume, dissolved in water (150 mL), 1N HCl was added to give a solution of pH 7, and extracted with chloroform (3 x 150 mL). The combined chloroform extracts were washed with saturated NaCl, dried over MgSO₄, and the solvent evaporated to give 5.7 g of a solid. This solid was recrystallized from absolute ethanol (75 mL), and vacuum dried at 50° C. for 3 days to give 2.59 g of 4-[4-[4-(10,11-dihydro-5H-dibenzo-[a,d]cyclohepten-5-ylidene)-1-piperidinyl]-1-hydroxybutyl]-α, α-dimethylbenzeneacetic acid, mp 135°-137° C.

EXAMPLE 27

Preparation of 4-[4-[4-(10,11-Dihydro-5H-dibenzo[a,d]cyclohepten-5-ylidene)-1-piperidinyl]-1-oxobutyl]-α, α-dimethylbenzeneacetic acid By procedures essentially the same as those described in Example 26, and by substituting 4-[4-[4-(10,11-dihydro-5H-dibenzo[a,d]cyclohepten-5-ylidene)-1-piperidinyl]-1-oxobutyl]-α, α-dimethylbenzeneacetic acid ethyl ester hydrobromide for 4-[4-[4-(10,11-dihydro-5H-dibenzo[a,d]cyclohepten-5-ylidene)-1-piperidinyl]-1-hydroxybutyl]-α, α-dimethylbenzeneacetic acid ethyl ester; the corresponding 4-[4-[4-(10,11-dihydro-5H-dibenzo[a,d]cyclohepten-5-ylidene)-1-piperidinyl]-1-oxobutyl]-α, α-dimethylbenzeneacetic acid, mp 122°-125° C. (ethanol), was prepared.

EXAMPLE 28

Preparation of 4-(10,11-Dihydro-5H-dibenzo[a,d]cyclohepten-5-ylidene)-1-[4-[4-(1,1-dimethyl-2-hydroxyethyl)phenyl]-4-hydroxybutyl]piperidine Method E To a stirred suspension of lithium aluminum hydride (1.16 g, 0.0305 mol) in tetrahydrofuran (150 mL) at 0° C. under nitrogen, was added dropwise a solution of 4-[4-[4(10,11-dihydro-5H-dibenzo[a,d]cyclohepten-5-ylidene)-1piperidinyl]-1-hydroxybutyl]-α, α-dimethylbenzeneacetic acid ethyl ester (8.2 g, 0.0153 mol) in tetrahydrofuran (80 mL). The reaction mixture was stirred at ambient temperature overnight and cooled to 0° C. Water (2.2 mL), 15% NaOH (2.2 mL) and water (6.6 mL) were carefully added. The mixture was warmed to ambient temperature, filtered through celite, and the solvent evaporated to give 7.8 g of a solid. This solid was recrystallized from 2-propanol and vacuum dried at 50° C. for 60 hours to provide 4.11 g of 4-(10,11-dihydro-5H-dibenzo[a,d]cyclohepten-5-ylidene)-1-[4-[4-(1,1-dimethyl-2-hydroxyethyl)phenyl]-4-hydroxybutyl]piperidine, mp 157°-159° C.

EXAMPLE 29

Preparation of 6-[4-(10,11-Dihydro-5H-dibenzo[a,d]cyclohepten-5-ylidene)-1-piperidinyl]-N-(2-phenylethyl)hexanamine dihydrochloride By procedures essentially the same as those described in Example 3, and by substituting 6-oxo-6-(2-phenyethyl)-amino]hexanoic acid for 4-[4-(1,1-dimethylethyl)-phenyl]-butanoic acid; the corresponding 6-[4-(10,11-dihydro-5H-dibenzo[a,d]cyclohepten-5-ylidene)-1-piperidinyl]-N-(2-phenylethyl)hexanamine dihydrochloride, mp 255°-256° C. (methanol, 2-propanol, ethyl acetate), was prepared.

What is claimed is:
1. A compound having the formula

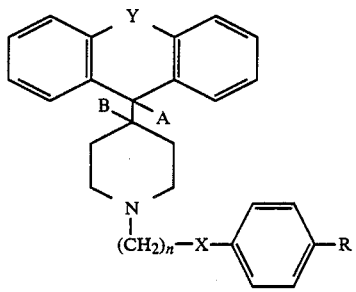

wherein
- n is a positive whole integer from 3 to 6;
- y is —CH$_2$O—, —CH$_2$CH$_2$—or —CH=CH—;
- A is hydroxy and B is hydrogen, or A and B taken together form a second bond between the carbons to which they are attached;
- X is —CH(OH)—, —C(=O)—, —S—, —NH—, —O—, or —NHCH$_2$CH$_2$—; and
- R is hydrogen, tert-butyl, —C(CH$_3$)$_2$CH$_2$OH, —C(CH$_3$)$_2$CO$_2$H, or —C(CH$_3$)$_2$COOalkyl wherein alkyl is a chain having 1 to 4 carbons, provided that when R is hydrogen X is —NHCH$_2$CH$_2$—, each enantiomeric or diastereomeric form thereof, or a pharmaceutically acceptable acid addition salt thereof.

2. A compound as in claim 1 where n is 3, Y is —CH$_2$CH$_2$—, X is —CH(OH)—, and R is tert-butyl.

3. A compound as in claim 2 where A is hydroxy and B is hydrogen.

4. A compound as in claim 2 where A and B join to form a bond.

5. A compound of claim 1, 4-[4-(5H-dibenz a,d]cyclohepten-5-ylidene)-1-piperidinyl]-1-[4-(1,1-dimethylethyl)phenyl]-1-butanone maleate.

6. A compound of claim 1, 6-[4-(10,11-dihydro-5H-dibenzo-[a,d]cyclohepten-5-ylidene)-1-piperidinyl]-1-[4-(1,1-dimethylethyl)phenyl]-1-hexanone fumarate.

7. A compound of claim 1, 4-[4-[4-(10,11-dihydro-5H-dibenzo[a,d]cyclohepten-5-ylidene)-1-piperidinyl]-1-hydroxybutyl]-α, α-dimethylbenzeneacetic acid.

* * * * *